(12) United States Patent
Montakhabi

(10) Patent No.: US 7,694,819 B2
(45) Date of Patent: Apr. 13, 2010

(54) DISPOSABLE URINARY DEVICE AND DISPENSER

(75) Inventor: Saeid Montakhabi, Herndon, VA (US)

(73) Assignee: E Z P, Herndon, VA (US)

(*) Notice: Subject to any disclaimer, the term of this patent is extended or adjusted under 35 U.S.C. 154(b) by 86 days.

(21) Appl. No.: 11/960,797

(22) Filed: Dec. 20, 2007

(65) Prior Publication Data
US 2009/0159470 A1  Jun. 25, 2009

(51) Int. Cl.
B65D 21/02 (2006.01)
A47K 11/00 (2006.01)
A47F 1/08 (2006.01)

(52) U.S. Cl. ................. 206/499; 4/144.2; 4/144.3; 4/144.4; 221/305

(58) Field of Classification Search .......... 206/499; 4/144.1–144.4; D24/122; 221/302–309
See application file for complete search history.

(56) References Cited

U.S. PATENT DOCUMENTS

| | | | |
|---|---|---|---|
| 2,689,062 A * | 9/1954 | Brown | 206/499 |
| 2,771,216 A * | 11/1956 | Reiner | 206/499 |
| 2,878,486 A | 3/1959 | Bartlett et al. | |
| 2,991,910 A * | 7/1961 | Coe | 206/499 |
| 3,171,136 A * | 3/1965 | Gibson | 4/144.4 |
| 3,306,515 A | 2/1967 | Beaumont | |
| 3,731,869 A | 5/1973 | Griffin | |
| 3,964,111 A * | 6/1976 | Packer | 4/144.4 |
| 4,023,216 A | 5/1977 | Li | |
| 4,108,222 A | 8/1978 | Kaufman | |
| 4,163,508 A | 8/1979 | Mannor | |
| 4,304,013 A | 12/1981 | Heimreid | |
| 4,531,245 A | 7/1985 | Lowd et al. | |
| 4,608,046 A | 8/1986 | Towfigh | |
| 4,681,573 A | 7/1987 | McGovern et al. | |
| 4,751,751 A | 6/1988 | Reno | |
| 4,937,890 A | 7/1990 | Tafur | |
| 5,091,998 A | 3/1992 | Witzke | |
| 5,199,601 A * | 4/1993 | Roethel | 221/302 |
| 5,201,869 A | 4/1993 | Roethel | |
| 5,222,628 A * | 6/1993 | Roethel | 221/307 |
| 5,243,712 A | 9/1993 | Cross | |
| 5,333,330 A | 8/1994 | Murtagh | |
| 5,370,637 A | 12/1994 | Brodeur | |
| 5,408,703 A | 4/1995 | Cicio | |
| D374,281 S | 10/1996 | Markles | |
| D379,225 S * | 5/1997 | Canahuate et al. | D24/122 |
| D393,061 S | 3/1998 | Mandich et al. | |
| 5,742,948 A | 4/1998 | Cicio | |

(Continued)

OTHER PUBLICATIONS

Urinelle, *A Question of Hygiene and Health*, p. 1-6, Admitted Prior Art.

*Primary Examiner*—Bryon P Gehman
(74) *Attorney, Agent, or Firm*—Capitol City TechLaw

(57) ABSTRACT

Disposable urinary devices may be arranged in a nested stack and enclosed within a dispenser. Each of the urinary devices may include body that tapers from an inlet opening having a curled edge to an outlet opening. The dispenser may provide an enclosure which permits the stacked urinary devices to be transported without damage during ordinary handling and to provide a sanitary covering for the urinary devices during storage. The dispenser also includes a retainer to allow the urinary devices to be withdrawn one by one, while providing a sanitary storage enclosure for the remaining urinary devices.

11 Claims, 6 Drawing Sheets

U.S. PATENT DOCUMENTS

| | | |
|---|---|---|
| D394,989 S | 6/1998 | Block |
| 5,893,176 A | 4/1999 | Magiera et al. |
| 5,966,748 A | 10/1999 | Young et al. |
| 5,991,932 A | 11/1999 | Wagner |
| 6,202,225 B1 | 3/2001 | Beck et al. |
| D447,232 S | 8/2001 | Hernandez-Fumero |
| D449,105 S * | 10/2001 | Azo ......................... D24/122 |
| 6,327,716 B1 | 12/2001 | Kaus |
| 6,434,757 B1 | 8/2002 | Filsouf |
| 6,460,200 B1 | 10/2002 | Mottale et al. |
| 6,475,198 B1 | 11/2002 | Lipman et al. |
| 6,719,741 B2 | 4/2004 | Ching |
| D495,798 S | 9/2004 | Gugliotta |
| D499,482 S | 12/2004 | Gugliotta |
| 6,966,454 B2 | 11/2005 | Kawolics et al. |
| 7,131,149 B2 | 11/2006 | Langford |
| D602,156 S * | 10/2009 | Young ...................... D24/122 |
| 2002/0193762 A1 | 12/2002 | Suydam |
| 2005/0097662 A1 | 5/2005 | Leimkuhler |
| 2009/0089919 A1* | 4/2009 | Rudolph .................... 4/144.4 |

* cited by examiner

DISPOSABLE URINARY DEVICE AND DISPENSER

BACKGROUND

1. Field

Example embodiments relate in general to a disposable urinary device, and more particularly to an improved disposable urinary device and a dispenser.

2. Description of Related Art

A woman may desire to urinate in a standing position for a variety of reasons, e.g., health, sanitation, convenience, etc. This has precipitated the development of a variety of urinary devices.

Some conventional urinary devices are presented as flat sheets (and sometimes as flat folded sheets) of material. Because the device is flat, it can be discretely carried by the woman, and therefore available at all times. The flat sheets may be packaged individually or a plurality of flat sheets may be provided in a dispenser. In any event, the flat sheet must be formed into a funnel shape prior to use. Furthermore, during use, pressure must be carefully maintained around the exterior of the device to keep the device open.

Other conventional urinary devices are preformed. These devices tend to be more rigid, bulky, complex, expensive to manufacture, and sometimes require assembly prior to use. Such devices are packaged individually and intended for repeated use.

SUMMARY

According to an example, non-limiting embodiment, a disposable urinary device may include a tapered body defining a passage. The tapered body may have a first end with a curled edge defining an inlet opening of the passage. The tapered body may have a second end with an edge defining an outlet opening of the passage. The outlet opening may be smaller than the inlet opening. The tapered body is not creased or scored and does not include any fold marks.

According to another example, non-limiting embodiment, a dispenser in combination with a stack of disposable urinary devices may include a tubular housing. A stack of disposable urinary devices may be provided in the tubular housing. Each of the disposable urinary devices may include a tapered body defining a passage. The tapered body may have a first end with a curled edge defining an inlet opening of the passage. The tapered body may have a second end with an edge defining an outlet opening of the passage. The outlet opening may be smaller than the inlet opening. The tapered body is not creased or scored and does not include any fold marks. A retainer may be provided in the tubular housing. The retainer may abut against the curled edge of the inlet opening of one of the disposable urinary devices.

The above and other features of example embodiments including various and novel details of construction and combinations of parts will now be more particularly described with reference to the accompanying drawings. It will be understood that the details of the example embodiments are shown by way of illustration only and not as limitations of the invention. The principles and features of this invention may be employed in varied and numerous embodiments without departing from the spirit and scope of the invention.

BRIEF DESCRIPTION OF THE DRAWINGS

Example, non-limiting embodiments will become more fully understood from the detailed description below and the accompanying drawings, wherein like elements are represented by like reference numerals, which are given by way of illustration only and thus are not limiting of the present invention.

DESCRIPTION OF EXAMPLE, NON-LIMITING EMBODIMENTS

Figure 1:
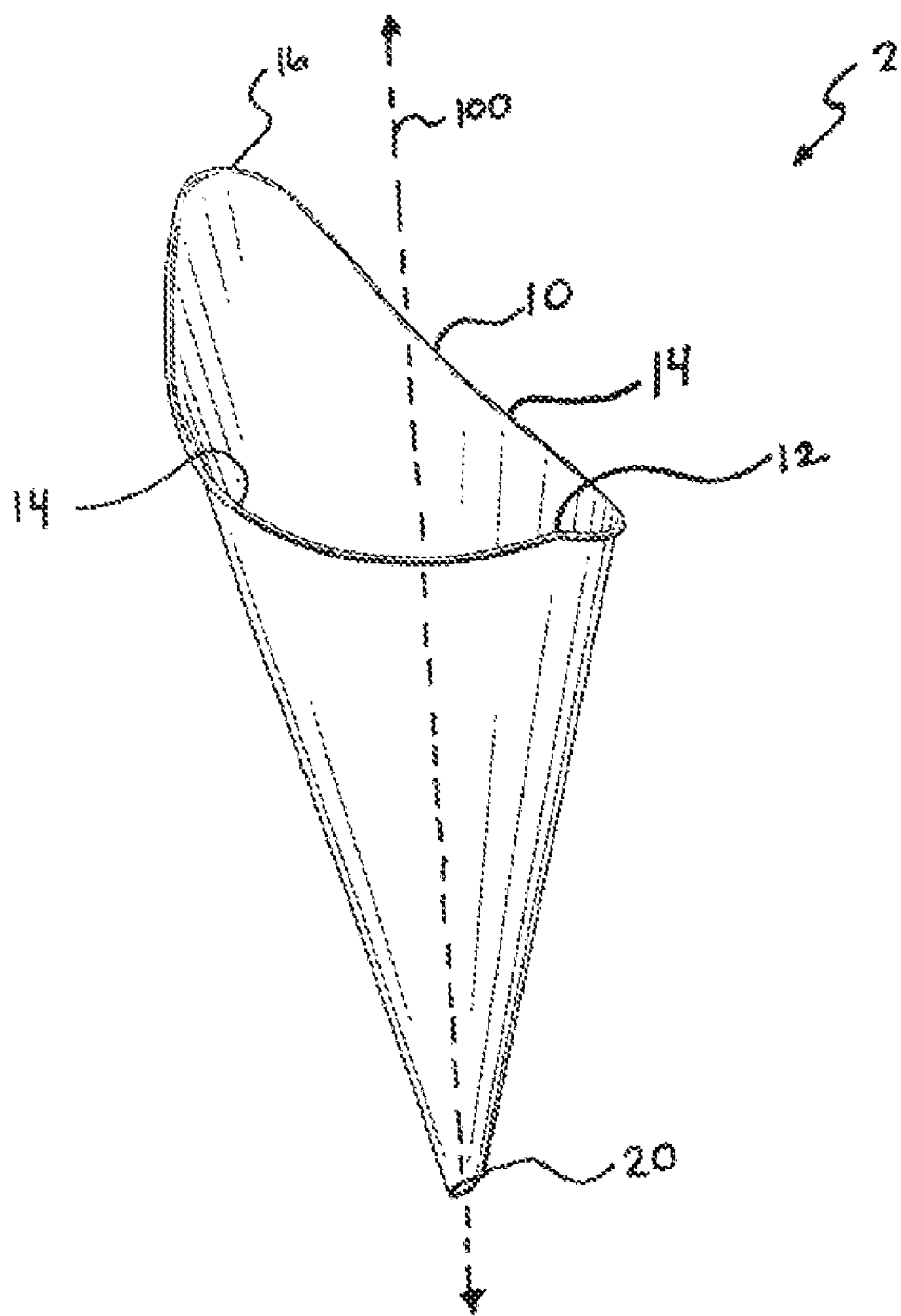
FIG. 1 is a perspective view of a disposable urinary device according to example, non-limiting embodiment.

I. Example Disposable Urinary Device—FIGS. 1-4:

As shown, an example, non-limiting embodiment of a disposable urinary device 2 is in the form of a funnel that tapers from a larger upper opening 10 to a smaller lower opening 20. The device 2 tapers uniformly along its entire length. The device 2 has a circular shape in a cross-section taken perpendicular to the longitudinal axis 100 (see FIG. 1). The device 2 is formed without any creases or scores and without fold marks, which may increase structural integrity.

In alternative embodiments, the cross-sectional shape of the device may be something other than circular; the device may taper in a non-uniform fashion; and/or the device may be formed with creases and/or folds.

The larger upper opening 10 is contoured to provide a comfortable fit around the vulva when in use. For example, the upper opening 10 is defined by an edge having a front convex portion 12. The front convex portion 12 transitions downward to a pair of side concave portions 14. The side concave portions 14 transition upward to a rear convex portion 16. The edge of the upper opening 10 is curled (or rounded), which may increase the structural integrity of the device. At the same time, the curled edge makes the upper opening 10 more comfortable and reduces the likelihood of paper cut injuries when the device 2 is in use.

In alternative embodiments, the upper opening may be provided with numerous and varied contours. Also, the upper opening may or may not have a curled edge.

The lower opening 20 defines a plane that is inclined relative to the longitudinal axis 100 of the device 2. In alternative embodiments, the lower opening may be perpendicular to the longitudinal axis of the device 2.

Figure 2:
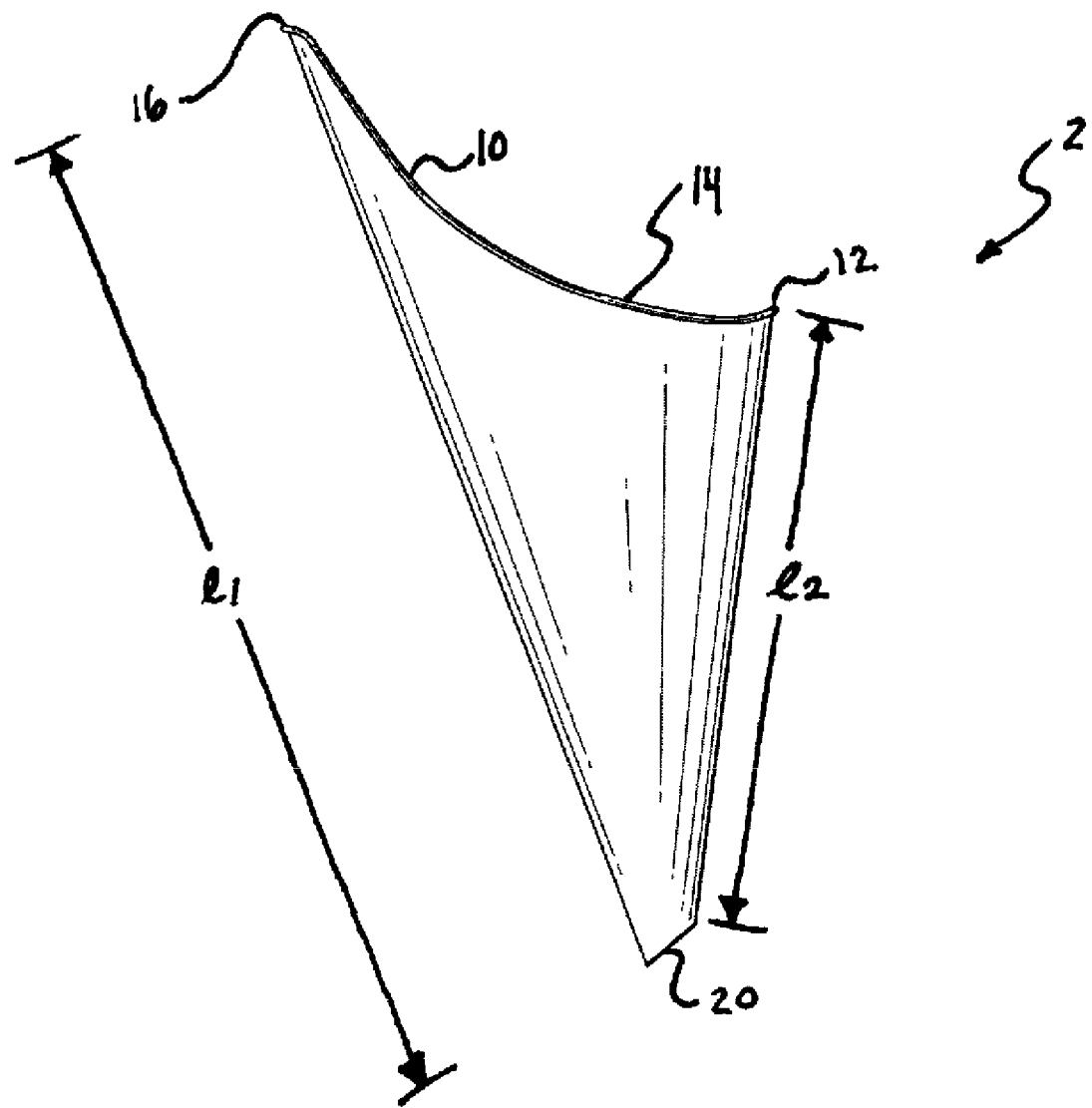
FIG. 2 is a right side elevation view of the disposable urinary device depicted in FIG. 1.
Figures 3, 4:
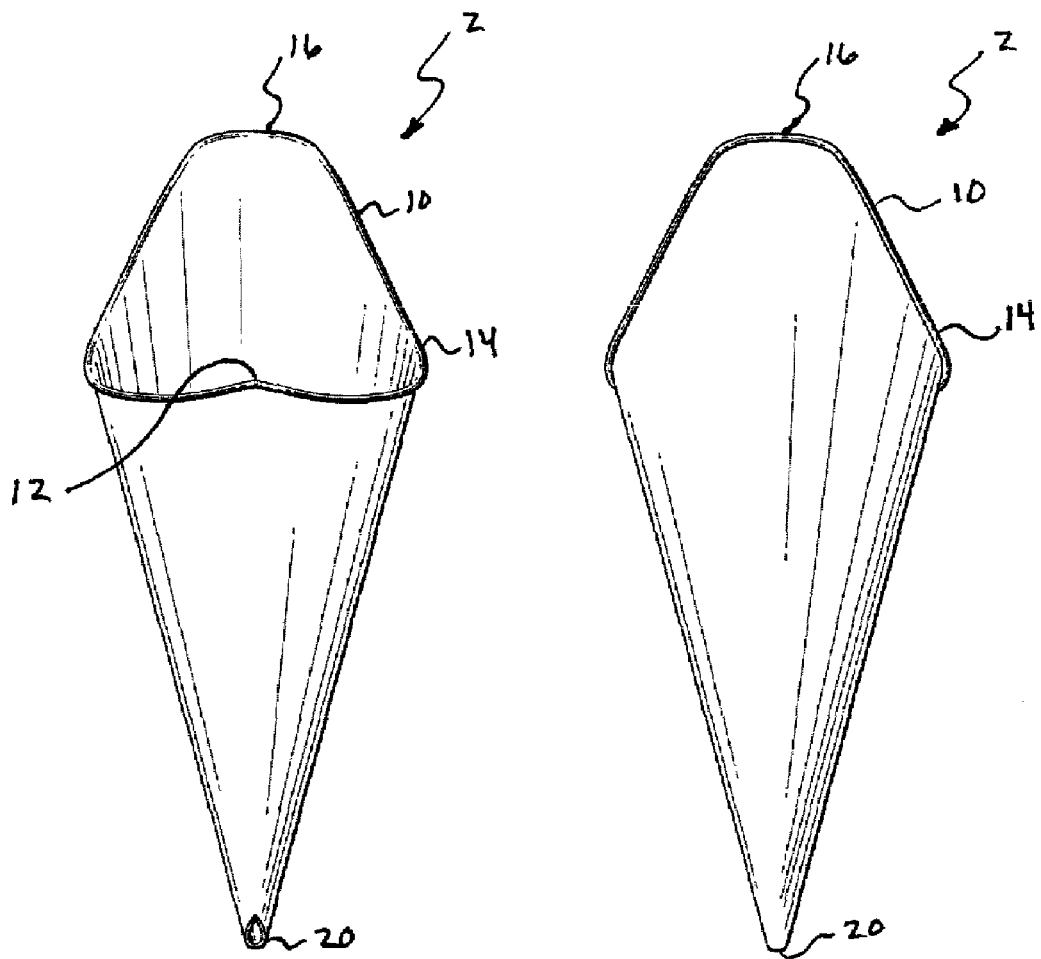
FIGS. 3 and 4 are front and rear elevation views, respectively, of the disposable urinary device depicted in FIG. 1.

With reference to FIG. 2, the distance "$l_1$" between the top of the rear convex portion 16 and the lower opening 20 is greater than the distance "$l_2$" between the top of the front convex portion 12 and the lower opening 20. At various points around the circumference of the device 2, the distances between the upper opening 10 and the lower opening 20 may be varied.

With the upper opening 10 placed around the outside of the woman's vulva, the woman may urinate from a standing position. Here, the device 2 is located with the front convex portion 12 facing forward. In this position, the portion of the device 2 spanning between the rear convex portion 16 and the lower opening 20 serves as a trough to focus the urine into a stream form. The incline of the lower opening 20 (relative to the longitudinal axis 100 of the device 2) provides for a clean discharge of the urine from the device 2.

The device 2 can be fabricated from numerous and varied materials. By way of example only, such materials include paper, cardboard and plastic like films. If the material is water-absorbent and/or water-dissolvable, then the inside surface of the device 10 may be provided with a moisture resistant coating (e.g., plastic or wax) to prevent the urine passing through the device 10 from effecting the structural integrity of the device 2.

II. Example Dispenser—FIGS. 5-9:

The disposable urinary devices 2 can be arranged in a nested stack and enclosed within a dispenser. The dispenser may serve as a shipping carton to provide an enclosure which permits the nested devices 2 to be transported without damage during ordinary handling and to provide a sanitary covering for the devices 2 during storage. The dispenser also includes features to allow the devices 2 to be withdrawn one by one, while providing a sanitary storage enclosure for the remaining devices 2.

Figure 5:
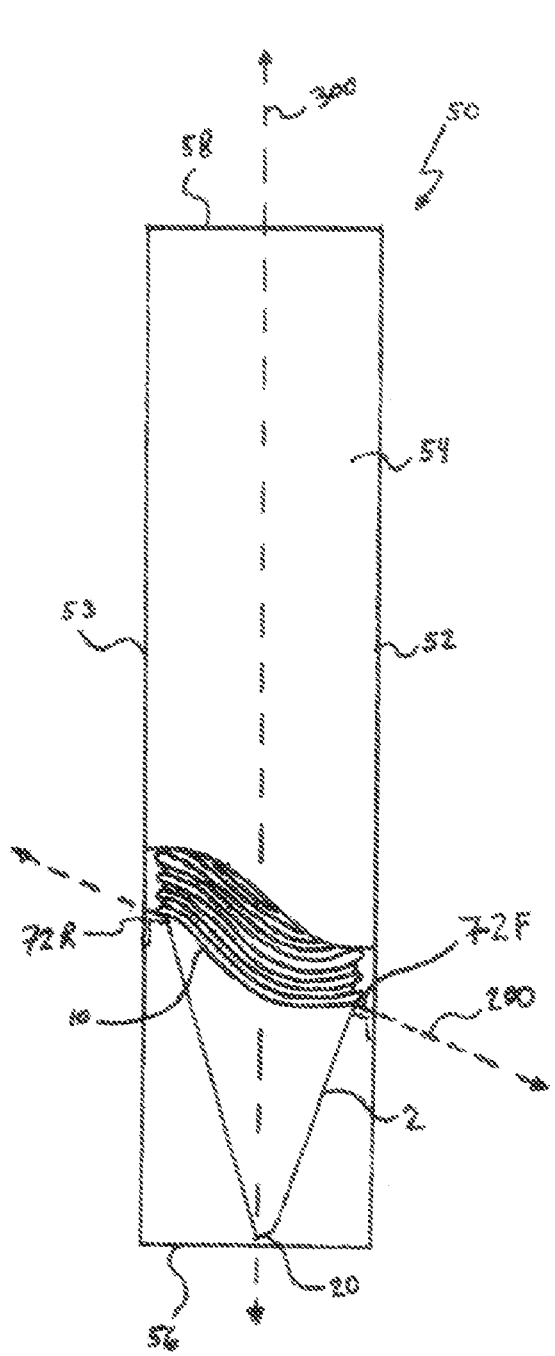
FIG. 5 is a left side elevation view of a dispenser according to an example, non-limiting embodiment.
Figure 6:
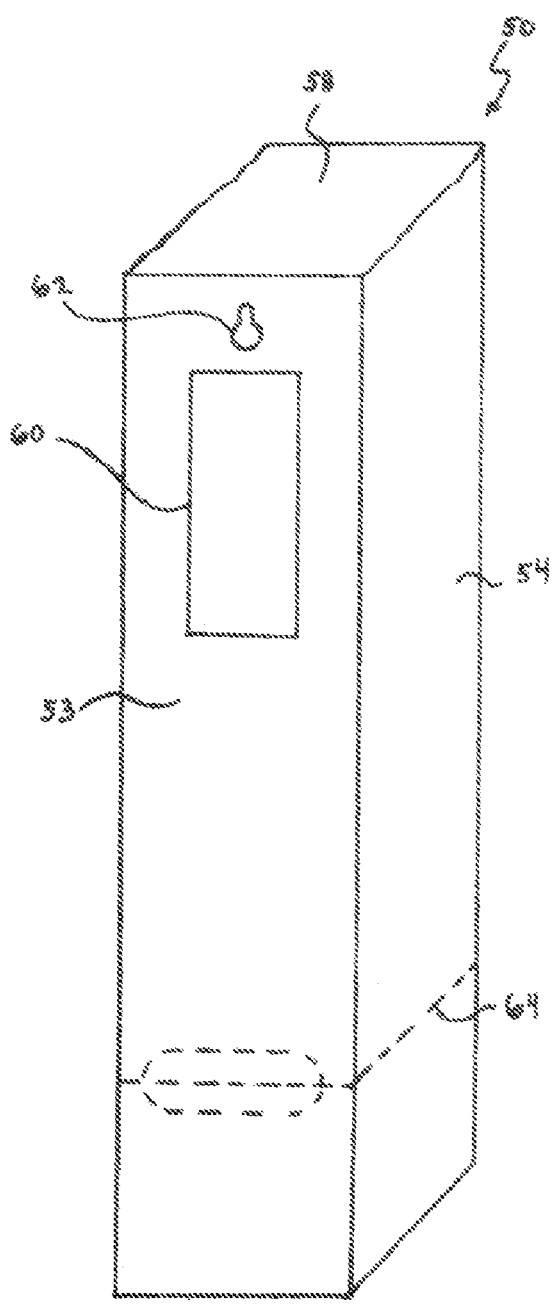
FIG. 6 is a perspective view of the dispenser depicted in FIG. 5.
Figure 7:
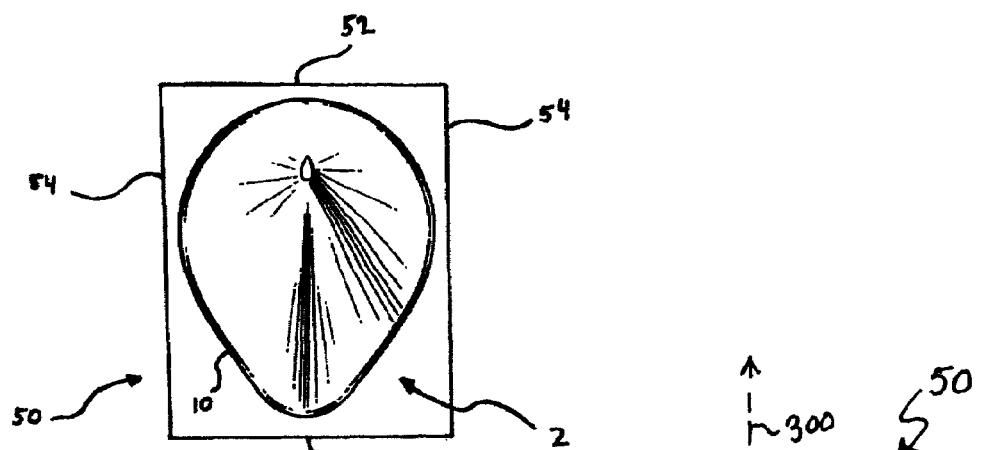
FIG. 7 is a schematic view of the dispenser depicted in FIG. 5.

FIGS. 5 and 6 depict an example, non-limiting embodiment of a dispenser 50. The dispenser 50 can be formed from a blank of sheet material (e.g., paperboard stock). The blank is folded and erected into a tubular carton that has a front panel 52, a rear panel 53, opposed side panels 54, a bottom closure panel 56 and a top closure panel 58. A stack of nested urinary devices 2 is inserted into the dispenser 50. Turning briefly to FIG. 7, the dispenser 50 has a rectangular cross-sectional shape that is slightly larger than the upper opening 10 of the nested urinary devices 2.

The dispenser 50 may be suspended for use. To this end, as shown in FIG. 6, an adhesive strip 60 is applied to the rear panel 53 for sticking or hanging the dispenser 50 on a wall. The adhesive strip 60 may be covered by a removable covering (not shown) to preserve the adhesive qualities of the adhesive strip 60 prior to use. The rear panel 53 also includes an opening 62 for engagement with a hook, a screw or a nail as an alternate means for suspending the dispenser 50 during use. In alternative embodiments, numerous and varied mechanisms, which are well known in this art, may be suitably implemented to suspend the dispenser 50 during use. The dispenser 50 may be removed from the wall and discarded when empty.

The front panel 52 may include a viewing window (not shown) that is covered by a clear transparent material. The viewing window provides an indication of the number of urinary devices 2 remaining in the dispenser 50.

The dispenser 50 is adapted to contain and dispense the disposable urinary devices 2. When placed in the dispenser 50, the urinary devices 2 are nested in a stack as shown in FIG. 5.

As shown in FIG. 6, the dispenser 50 includes a perforated tear line 64 that extends across the front panel 52, the rear panel 53 and the opposed side panels 54. The bottom portion of the dispenser 50 can be torn away along the perforated tear line 64 to expose the lower most urinary device 2 in the dispenser 50. It will be readily apparent that the perforated tear line 64 is provided below the upper opening 10 of the lower most urinary device 2 in the dispenser 50.

Turning back to FIG. 5, the dispenser 50 includes a retainer 70 that supports the stack of urinary devices 2 along the underside of the curled edge of the upper opening 10 of the lower most urinary device 2. As shown, the retainer 70 is located in the dispenser 50 above the bottom closure panel 56 a sufficient distance to keep the lower opening 20 of the lower most urinary device 2 spaced apart from the bottom closure panel 56. In this example embodiment, the retainer 70 is inclined (as shown by reference line 200) relative to the longitudinal axis 300 of the dispenser 50. In this regard, the retainer 70 does not define a plane that is perpendicular to the longitudinal axis of the dispenser 50.

Figure 8:
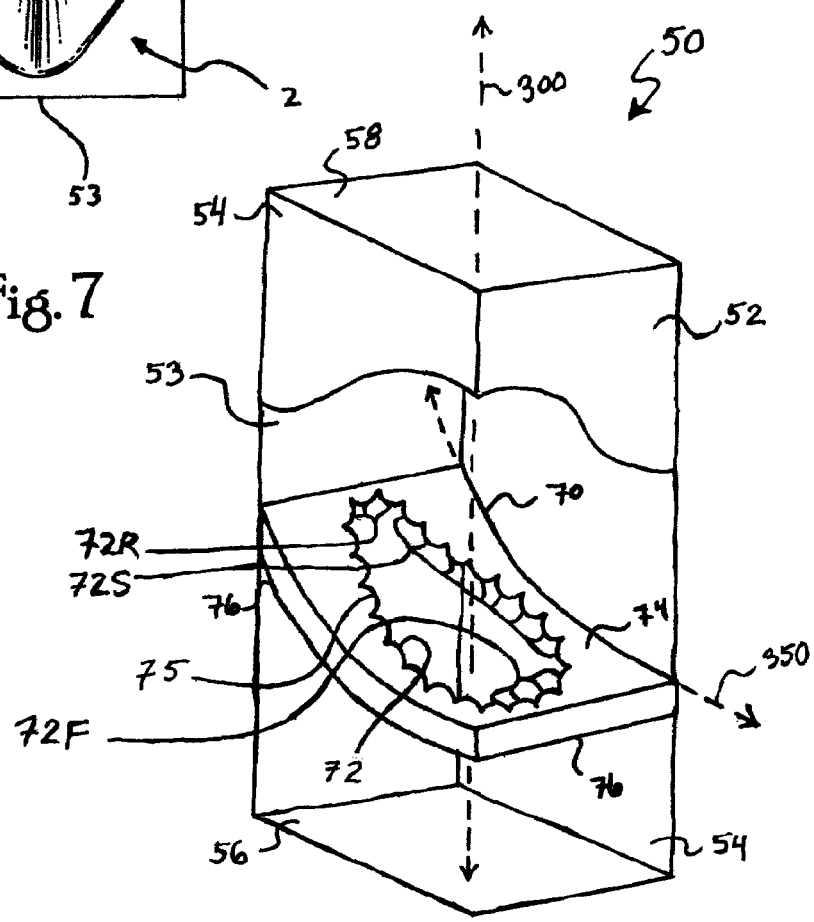
FIG. 8 is a perspective view of a retainer according to an example, non-limiting embodiment.
Figure 9:
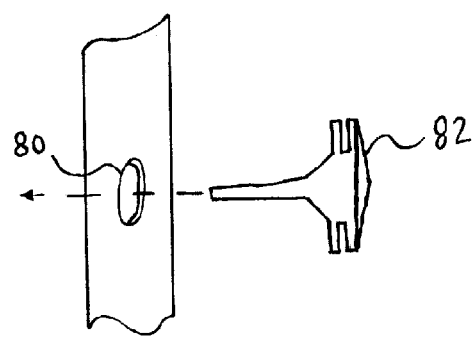
FIG. 9 is a schematic view of a retainer according to another example, non-limiting embodiment.

By way of example only, and with reference to FIG. 8, the retainer 70 may be in the form of an insert that is mounted in the dispenser 50. The retainer 70 may be fabricated from the same material as the dispenser 50. As shown, the retainer 70 has a dispensing panel 74, and mounting panels 76 extended from the dispensing panel 74. An adhesive can be applied to the outside surface of the mounting panels 76 for mounting the retainer 70 on the interior of the dispenser 50.

The dispensing panel 74 has a curved profile, and an opening 75 that corresponds to the shape of the upper opening 10 of the urinary device 2. The opening 75 is defined by a plurality of tabs 72. The tabs 72 support the stack of urinary devices 2 along the underside of the curled edge of the upper opening 10 of the lower most urinary device 2. Thus, the tabs 72 provide a front retainer portion 72F that supports the front convex portion 12 of the disposable urinary device 2, a rear retainer portion 72R that supports the rear convex portion 16 of the disposable urinary device 2, and side retainer portions 72S that support the side concave portions 14 of the disposable urinary device 2. As shown in FIGS. 5 and 8, the front retainer portion 72F is provided at a relatively lower longitudinal position of the tubular housing, while the rear retainer portion 72R is provided at a relatively higher longitudinal position of the tubular housing. And the side retainer portions 72S are provided along paths 350 that curve in a longitudinal direction of the tubular housing. The tabs 72 provide relatively rigid support for the weight of the nested stack of urinary devices 2, without yielding in the absence of external loading.

To remove a urinary device 2 from the nested stack enclosed by the dispenser 50, the bottom portion of the dispenser 50 is torn away along the perforated tear line 64. The exposed tapered sidewall of the lowermost urinary device 2 is grasped and drawn downwardly causing the tabs 72 to deflect sufficiently to allow the curled edge of the urinary device 2 to pass through the opening 75. After the lowermost urinary device 2 has been withdrawn, the tabs 72 return to their original undeflected position, to provide support for the next adjacent urinary device 2 in the nested stack.

In this example embodiment, the tabs 72 have a semicircular shape and are provided around the entire circumference of the opening 75. In alternative embodiments, the tabs may have some other geometrical shape and/or the tabs may be spaced apart from each other. The resiliency of the tabs can be adjusted by increasing and decreasing the length and/or shape of the tabs. In alternative embodiments, the dispensing panel can have a planar shape.

In the disclosed embodiment, the retainer is in the form of an insert. In alternative embodiments, the retainer may be in the form of a plurality of individual and spaced apart fingers. The fingers may be mounted on the front, rear and/or side panels of the dispenser 50. For example, with reference to FIG. 9, the panels of the dispenser 50 may include a mounting hole 80 into which a finger 82 is inserted. Each individual finger may extend in a perpendicular fashion relative to the longitudinal axis of the dispenser. However, some of the fingers may be spaced apart from each other in the longitudinal direction of the dispenser. In this regard, the fingers (or retainer) do not define a plane that is perpendicular to the longitudinal axis of the dispenser.

In the disclosed embodiment, the dispenser has a rectangular cross-sectional shape. In alternative embodiments, the dispenser may have some other geometric cross-sectional shape. For example, the dispenser may have a circular cross-sectional shape.

What is claimed is:

1. A dispenser in combination with a stack of disposable urinary devices, the combination comprising:
    a tubular housing;
    a stack of disposable urinary devices provided in the tubular housing, each of the disposable urinary devices including,
        a tapered body defining a passage;
        the tapered body having a first end with a curled edge defining an inlet opening of the passage; and
        the tapered body having a second end with an edge defining an outlet opening of the passage, the outlet opening being smaller than the inlet opening;
        wherein the tapered body is not creased or scored and does not include an fold marks; and
    a retainer provided in the tubular housing, the retainer abutting against the curled edge of the inlet opening of only a lower most disposable urinary device in the stack;
    wherein the retainer includes
        a front retainer portion provided at a relatively lower longitudinal position of the tubular housing,
        a rear retainer portion provided at a relatively higher longitudinal position of the tubular housing, and
        side retainer portions respectively provided along paths that curve in a longitudinal direction of the tubular housing, the paths extending between the front retainer portion and the rear retainer portion.

2. The combination of claim 1, wherein the retainer does not define a plane that is perpendicular to a longitudinal axis of the tubular housing.

3. The combination of claim 1, wherein the retainer is inclined relative to a longitudinal axis of the tubular housing.

4. The combination of claim 1, wherein the retainer is fixed to the tubular housing at varied locations in a longitudinal direction of the tubular housing.

5. The combination of claim 1, wherein the retainer is an insert mounted in the tubular housing, the insert having tabs that abut against the curled edge of the inlet opening of one of the disposable urinary devices.

6. The combination of claim 5, wherein the tabs have a semicircular shape.

7. The combination of claim 1, wherein the retainer is a plurality of fingers respectively inserted into holes provided in the tubular housing.

8. The combination of claim 1, wherein the ends of the tubular housing are closed by a top panel and a bottom panel.

9. The combination of claim 8, further comprising a perforated tear line provided on the tubular housing between the retainer and the bottom panel.

10. The combination of claim 1, wherein the tubular housing has a rectangular cross-sectional shape.

11. A dispenser in combination with a stack of urinary devices, the combination comprising:
    a tubular housing;
    a stack of urinary devices provided in the tubular housing; and
    a retainer provided in the tubular housing and abutting against at least one of the urinary devices in the stack;
    wherein the retainer includes
        a front retainer portion provided at a relatively lower longitudinal position of the tubular housing,
        a rear retainer portion provided at a relatively higher longitudinal position of the tubular housing, and
        side retainer portions respectively provided along paths that curve in a longitudinal direction of the tubular housing, the paths extending between the front retainer portion and the rear retainer portion.

* * * * *